United States Patent
Meyer et al.

(10) Patent No.: US 6,835,857 B2
(45) Date of Patent: Dec. 28, 2004

(54) PROCESS FOR THE MANUFACTURE OF 4-(6-BROMOHEXYLOXY)-BUTYLBENZENE

(75) Inventors: Oliver Meyer, Dorsheim (DE); Helmut Heitger, Ingelheim (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

(21) Appl. No.: 10/379,443

(22) Filed: Mar. 4, 2003

(65) Prior Publication Data

US 2003/0171620 A1 Sep. 11, 2003

Related U.S. Application Data

(60) Provisional application No. 60/386,280, filed on Jun. 6, 2002.

(30) Foreign Application Priority Data

Mar. 5, 2002 (DE) .......................... 102 09 583

(51) Int. Cl.[7] .............................................. C07C 41/09

(52) U.S. Cl. ...................................................... 568/663

(58) Field of Search ........................... 568/663; 564/346

(56) References Cited

FOREIGN PATENT DOCUMENTS

| EP | 1132373 A2 | 9/2001 |
|---|---|---|
| GB | 2140800 A | 12/1984 |
| WO | WO-9519336 A1 | 7/1995 |

OTHER PUBLICATIONS

Jones, Robert M. et al; Mutational Evidence for a Common K antagonist Binding Pocket in the Wild–Type K and Mutant u[K303E] Opioid Receptors; Journal of Medicinal Chemistry; 1998; pp. 4911–4914; vol. 41; No. 25.

Rong, Yajing et al; A New Synthetic Approach to Salmeterol; Synthetic Communications; 1999; pp. 2155–2162; vol. 29; No. 12.

*Primary Examiner*—Rosalynd Keys
(74) *Attorney, Agent, or Firm*—Robert P. Raymond; Michael Morris; David A. Dow

(57) ABSTRACT

The present invention relates to an improved process for preparing 4-(6-bromohexyloxy)-butylbenzene by reacting 4-phenylbutanol with 1,6-dibromohexane in the presence of a base and a phase transfer catalyst, wherein 4-phenylbutanol in a diluent is metered into a mixture consisting of 1,6-dibromohexane, a base, a phase transfer catalyst and a diluent, and the use of the 4-(6-bromohexyloxy)-butylbenzene thus prepared for producing salmeterol in a method known per se.

12 Claims, No Drawings

PROCESS FOR THE MANUFACTURE OF 4-(6-BROMOHEXYLOXY)-BUTYLBENZENE

RELATED APPLICATIONS

Benefit of U.S. Provisional Application Ser. No. 60/386,280, filed on Jun. 6, 2002 is hereby claimed, and said application is herein incorporated by reference.

The present invention relates to an improved process for the manufacture of 4-(6-bromohexyloxy)-butylbenzene by reacting 4-phenylbutanol with 1,6-dibromohexane in the presence of a base and a phase transfer catalyst, and the use of the 4-(6-bromohexyloxy)-butylbenzene thus prepared for producing salmeterol in a method known per se.

BACKGROUND TO THE INVENTION 4-(6-Bromohexyloxy)-butylbenzene is a valuable intermediate product for preparing the active substance salmeterol, which is used as a bronchodilator for treating asthma or chronic bronchitis.

According to the teaching of German patent application DE 34 14 752, 4-(6-bromohexyloxy)-butylbenzene is obtained by reacting 4-phenylbutanol with 1,6-dibromohexane with a sodium hydride dispersion as base. For safety reasons it is not really possible to carry out production on an industrial scale using sodium hydride dispersions.

European patent application EP 1 132 373 describes a laboratory process for producing 4-(6-bromohexyloxy)-butylbenzene in which a mixture consisting of 4-phenylbutanol, 1,6-dibromohexane, potassium hydroxide and tetrabutyl ammonium hydrogen sulphate is stirred for 20 hours at ambient temperature. However, this laboratory method cannot be carried out on an industrial scale as the reaction is strongly exothermic, leading to a sharp increase in the reaction temperature, producing residues which are difficult to stir and secondary products (elimination products) which lower the yield.

The aim of the present invention is thus to provide a process which makes it possible to prepare 4-(6-bromohexyloxy)-butylbenzene in good yields on an industrial scale while avoiding the drawbacks which occur with the processes known from the prior art.

DETAILED DESCRIPTION OF THE INVENTION

Surprisingly, it has now been found that 4-(6-bromohexyloxy)-butylbenzene can be prepared in good yields and on an industrial scale by reacting 4-phenylbutanol with 1,6-dibromohexane in the presence of a base and a phase transfer catalyst if 4-phenylbutanol in a diluent is added to a mixture comprising or consisting of 1,6-dibromohexane, a base, a phase transfer catalyst and a diluent.

The invention thus relates to an improved process for preparing 4-(6-bromohexyloxy)-butylbenzene by reacting 4-phenylbutanol with 1,6-dibromohexane in the presence of a base and a phase transfer catalyst, in which 4-phenylbutanol in a diluent is metered into a mixture consisting of 1,6-dibromohexane, a base, a phase transfer catalyst and a diluent.

The invention further relates to the use of the 4-(6-bromohexyloxy)-butylbenzene prepared by the process according to the invention for producing salmeterol in a manner known per se.

Preferred embodiments of the process according to the invention are processes wherein:

(A) the base used is an alkali metal hydroxide such as lithium hydroxide, sodium hydroxide or potassium hydroxide, particularly powdered potassium hydroxide;

(B) the phase transfer catalyst (PTC) used is a tetraalkylammonium or tetraalkylphosphonium salt, wherein the alkyl groups may be identical or different, such as for example salts of tetraoctylammonium, methyltrioctylammonium, tetramethylammonium, tetraethylammonium, tetrahexylammonium Aliquat 175 (tributylmethylammonium) or Aliquat 336 (methyltrioctylammonium). Preferably, the PTC is a tetraalkylammonium halide, a tetraalkylammonium sulphate, a tetraalkylammonium hydrogen sulphate, a tetraalkylammonium nitrate or a tetraalkylammonium phosphate, more particularly a tetraalkylammonium hydrogen sulphate, most preferably tetra-n-butylammonium hydrogen sulphate.

The term "alkyl" as used above and hereinafter in connection with the phase transfer catalyst comprises straight-chain and branched alkyl groups with 1 to 8, preferably 2 to 6, more particularly 4 carbon atoms. Thus, preferred alkyl groups are the ethyl, n-propyl, i-propyl, n-butyl, 2-butyl, tert-butyl, n-pentyl, 2-pentyl, neo-pentyl, n-hexyl and 2-hexyl group. The n-butyl group is most particularly preferred.

Other preferred embodiments of the process according to the invention are processes wherein:

(C) the diluent used is an aromatic hydrocarbon, preferably benzene, toluene or xylene, particularly toluene, or an optionally halogenated aliphatic hydrocarbon, preferably dichloromethane, chloroform, carbon tetrachloride or dichloroethane, particularly dichloromethane;

(D) the reaction is carried out in a temperature range from −10° C. to +30°, preferably from 0° C. to 28° C., particularly from 20 to 25° C.;

(E) the 4-phenylbutanol is added within 10 to 240 minutes, preferably 15 to 60 minutes, and the resulting reaction mixture is stirred for a further 30 to 180, preferably 45 to 150 minutes;

(F) 0.75 to 2.5 equivalents, preferably 1.5 to 2.2 equivalents, more particularly about 2 equivalents of 1,6-dibromohexane are used, based on 1 equivalent of 4-phenylbutanol;

(G) 2.5 to 5.5 equivalents, preferably 2.8 to 5.2 equivalents, more particularly 3.0 to 4.0 equivalents of base are used, based on 1 equivalent of 4-phenylbutanol;

(H) 0.01 to 0.5 equivalents, preferably 0.02 to 0.2 equivalents, more particularly 0.05 to 0.15 equivalents of phase transfer catalyst are used based on 1 equivalent of 4-phenylbutanol;

(I) the mixture of 1,6-dibromohexane, a base, a phase transfer catalyst and a diluent contains 1.5 to 4.0 parts by volume, preferably 2.0 to 3.0 parts by volume, more particularly 2.2 to 2.8 parts by volume of diluent, based on 1 part by volume of 1,6-dibromoehexane;

(J) the mixture of 4-phenylbutanol and diluent contains 1.5 to 10 parts by volume, preferably 2.0 to 6.0 parts by volume, more particularly 3.0 to 5.0 parts by volume of diluent, based on 1 part by volume of 4-phenylbutanol;

(K) after the reaction has ended water is added to the reaction mixture, the phases are separated, the organic phase is washed with water, concentrated under reduced pressure and the residue is fractionally distilled under a high vacuum.

In a particularly preferred embodiment 1 equivalent of 4-phenylbutanol in about twice the volume of toluene is metered, within 10 to 60 minutes, into a mixture of about 2 equivalents of 1,6-dibromohexane, 3 to 5 equivalents of KOH, about 0.1 equivalents of tetra-n-butylammonium hydrogen sulphate and 4 to 6 times the volume of toluene, based on the volume of 4-phenylbutanol, at a temperature between 20 and 30° C., with stirring. After it has all been added the mixture is rinsed with toluene and stirred for 90 to 360, preferably about 180 to 240 minutes at a temperature between 20 and 30° C. Then water is added, the organic phase is separated off and washed with water. The organic phase is concentrated and the residue is fractionally distilled under a high vacuum.

Further advantageous aspects of the procedure according to the invention are the high space-time yield of the present process as well as the high yield and purity of 4-(6-bromohexyloxy)-butylbenzene, which can be further processed directly or after distillation to form salmeterol.

Starting from the 4-(6-bromohexyloxy)-butylbenzene prepared by the process according to the invention, salmeterol is prepared in a manner known per se as described, for example, in DE 34 14 752 or EP 1 132 373.

The following Examples serve to illustrate some processes carried out by way of example for preparing 4-(6-bromohexyloxy)-butylbenzene. They are to be regarded merely as possible procedures described by way of example without restricting the invention to their content.

EXAMPLE 1

4-(6-Bromohexyloxy)-butylbenzene

At a temperature between 20 and 25° C., with stirring, a mixture of 247.5 ml (1.65 mol) of 4-phenylbutanol and 500 ml of toluene are added within 45 minutes to a mixture of 509.6 ml (3.3 mol) of 1,6-dibromohexane, 402 g of powdered (6.1 mol KOH) caustic potash, 5.6 g (0.165 mol) tetra-n-butylammonium hydrogen sulphate and 1250 ml of toluene.

After it has all been added, the mixture is rinsed with 125 ml of toluene and stirred for a further 2.5 hours at a temperature between 20 and 25° C. Then 1875 ml of water are added, the organic phase is separated off and washed twice with 1250 ml of water. The organic phase is evaporated down under reduced pressure using the rotary evaporator and the residue is fractionally distilled under a high vacuum (p<0.1 mbar). 408.5 g (79% of theory) of the title compound are obtained as a colorless oil.

EXAMPLE 2

4-(6-bromohexyloxy)-butylbenzene

A mixture of 10 ml (0.0655 mol) of 4-phenylbutanol and 20 ml of toluene is added within 15 minutes, with stirring, to a mixture of 20.2 ml (0.131 mol) of 1,6-dibromohexane, 16 g of powdered (0.242 mol KOH) caustic potash, 2.2 g (0.0066 mol) tetra-n-butylammonium hydrogen sulphate and 50 ml of toluene, at a temperature between 25 and 30° C. After it has all been added the mixture is rinsed with 5 ml of toluene and stirred for 2 hours at a temperature between 25 and 30° C. Then 75 ml of water are added, the organic phase is separated off and washed twice with 50 ml of water. The organic phase is concentrated under reduced pressure using the rotary evaporator and the residue is fractionally distilled under a high vacuum (p<0.1 mbar). 14.62 g (71% of theory) of the title compound are obtained as a colorless oil.

COMPARISON EXAMPLE 1

4-(6-bromohexyloxy)-butylbenzene (corresponding to EP 1 132 373)

To a mixture of 5 ml (0.0323 mol) of 4-phenylbutanol and 10.1 ml (0.0657 mol) of 1,6-dibromohexane are added, with stirring, 8 g of powdered (0.121 mol of KOH) caustic potash, whereupon the temperature rises to about 30° C. Then 1.1 g (0.0033 mol) of tetra-n-butylammonium hydrogen sulphate are added, whereupon the temperature rises to about 65° C.

After it has all been added the mixture is stirred for 20 hours at ambient temperature. The reaction mixture is filtered, the filtrate is taken up in 50 ml of diethylether and 50 ml of water are added. The organic phase is separated off and dried. The organic phase is evaporated down under reduced pressure using the rotary evaporator and the residue is fractionally distilled under a high vacuum (<0.1 mbar). 5.8 g (56% of theory) of the title compound are obtained as a colourless oil.

COMPARISON EXAMPLE 2

4-(6-bromohexyloxy)-butylbenzene

To a mixture of 20.2 ml (0.131 mol) of 1,6-dibromohexane, 16 g of powdered (0.242 mol KOH) caustic pot acid and 2.2 g (0.0066 mol) of tetra-n-butylammonium hydrogen sulphate are added 10 ml (0.0655 mol) of 4-phenylbutanol within 15 minutes, with stirring, at a temperature between 20 and 30° C. The reaction was spontaneously exothermic and the temperature could hardly be controlled. Towards the end of the addition, hard lumps were formed and the reaction mixture was impossible to stir.

We claim:

1. Improved process for preparing 4-(6-bromohexyloxy)-butylbenzene comprised of the steps of reacting 4-phenylbutanol with 1,6-dibromohexane in the presence of KOH and a phase transfer catalyst, wherein the 4-phenylbutanol in a diluent is metered within 10 to 240 minutes into a mixture comprised of 1,6-dibromohexane, a base, a phase transfer catalyst and a diluent and the resulting reaction mixture is stirred for a further 30 to 180 minutes and thereafter the 4-(6-bromohexyloxy)-butylbenzene product is isolated.

2. Process according to claim 1, wherein the phase transfer catalyst is tetraalkylammonium or tetraalkylphosphonium salt.

3. Process according to claim 1, wherein the phase transfer catalyst is tetraalkylammonium hydrogen sulphate.

4. Process according to claim 1, wherein the diluent is an aromatic hydrocarbon or an optionally halogenated aliphatic hydrocarbon.

5. Process according to claim 1, wherein the diluent is toluene or dichloromethane.

6. Process according to claim 1, wherein the reaction is carried out in a temperature range from −10° C to +30° C.

7. Process according to claim 1, wherein 0.75 to 2.5 equivalents of 1,6-dibromohexane are used, based on 1 equivalent of 4-phenylbutanol.

8. Process according to claim 1, wherein 2.5 to 5.5 equivalents of base are used, based on 1 equivalent of 4-phenylbutanol.

9. Process according to claim 1, wherein 0.01 to 0.5 equivalents of phase transfer catalyst are used, based on 1 equivalent of 4-phenylbutanol.

10. Process according to claim 1, wherein the mixture of 1,6-dibromohexane, base, phase transfer catalyst and diluent contains 1.5 to 4.0 parts by volume of diluent, based on 1 part of 1,6-dibromohexane.

11. Process according to claim 1, wherein the mixture of 4-phenylbutanol and diluent contains 1.5 to 10 parts by volume of diluent, based on 1 part of 4-phenylbutanol.

12. Process according to claim 1, wherein after the reaction has ended water is added to the reaction mixture, the phases are separated, the organic phase is washed with water, concentrated under reduced pressure and the residue is fractionally distilled under high vacuum.

* * * * *